(12) United States Patent
Whitman

(10) Patent No.: US 8,262,560 B2
(45) Date of Patent: Sep. 11, 2012

(54) IMAGING DEVICE FOR USE WITH A SURGICAL DEVICE

(75) Inventor: Michael P. Whitman, New Hope, PA (US)

(73) Assignee: Tyco Healthcare Group LP, Mansfield, MA (US)

( * ) Notice: Subject to any disclaimer, the term of this patent is extended or adjusted under 35 U.S.C. 154(b) by 425 days.

(21) Appl. No.: 10/127,310

(22) Filed: Apr. 22, 2002

(65) Prior Publication Data

US 2002/0165444 A1  Nov. 7, 2002

Related U.S. Application Data

(60) Provisional application No. 60/285,193, filed on Apr. 20, 2001, provisional application No. 60/300,107, filed on Jun. 22, 2001, provisional application No. 60/344,648, filed on Dec. 31, 2001.

(51) Int. Cl.
*A61B 1/05* (2006.01)

(52) U.S. Cl. ......... 600/112; 600/104; 600/109; 600/129

(58) Field of Classification Search .................. 348/373; 600/104, 109, 111, 112, 105, 129, 130, 166, 600/175, 114

See application file for complete search history.

(56) References Cited

U.S. PATENT DOCUMENTS

| | | |
|---|---|---|
| 3,858,577 A | 1/1975 | Bass et al. |
| 3,859,986 A | 1/1975 | Okada et al. |
| 4,027,510 A | 6/1977 | Hiltebrandt |
| 4,085,756 A | 4/1978 | Weaver |
| 4,198,960 A | 4/1980 | Utsugi |
| 4,250,873 A | 2/1981 | Bonnet |
| 4,273,109 A | 6/1981 | Enderby |
| 4,273,111 A | 6/1981 | Tsukaya |
| 4,286,585 A | 9/1981 | Ogawa |
| 4,367,729 A | 1/1983 | Ogiu |
| 4,379,457 A | 4/1983 | Gravener et al. |
| 4,402,311 A | 9/1983 | Hattori |
| 4,445,892 A | 5/1984 | Hussein et al. |
| 4,448,188 A | 5/1984 | Loeb |
| 4,494,549 A | 1/1985 | Namba et al. |
| 4,499,895 A | 2/1985 | Takayama |
| 4,559,928 A | 12/1985 | Takayama |
| 4,573,450 A * | 3/1986 | Arakawa ...................... 600/104 |
| 4,593,679 A | 6/1986 | Collins |
| 4,672,961 A | 6/1987 | Davies |
| 4,674,515 A | 6/1987 | Andou et al. |
| 4,732,156 A | 3/1988 | Nakamura |

(Continued)

FOREIGN PATENT DOCUMENTS

DE  42 13 426  10/1992

(Continued)

OTHER PUBLICATIONS

New York Magazine, The Best Doctors in New York, p. 80, Jun. 10, 2002.

(Continued)

*Primary Examiner* — John P Leubecker

(57) ABSTRACT

A surgical imaging device is provided, including a housing configured to couple to an outer surface of a surgical device and an image capture arrangement configured to generate image data; the surgical imaging device may also include a circuit arrangement disposed within the housing and electrically coupled to the camera arrangement, in which the circuit arrangement is configured to communicate the image data to at least one remote device.

33 Claims, 12 Drawing Sheets

U.S. PATENT DOCUMENTS

| | | | |
|---|---|---|---|
| 4,742,815 A | 5/1988 | Ninan et al. | |
| 4,756,309 A | 7/1988 | Sachse et al. | |
| 4,759,348 A * | 7/1988 | Cawood | 600/102 |
| 4,760,840 A | 8/1988 | Fournier, Jr. et al. | |
| 4,815,469 A | 3/1989 | Cohen et al. | |
| 4,819,632 A | 4/1989 | Davies | |
| 4,880,015 A | 11/1989 | Nierman | |
| 4,890,602 A | 1/1990 | Hake | |
| 4,893,613 A | 1/1990 | Hake | |
| 4,907,588 A | 3/1990 | Burston | |
| 4,907,973 A | 3/1990 | Hon | |
| 4,928,699 A | 5/1990 | Sasai | |
| 4,930,494 A | 6/1990 | Takehana et al. | |
| 4,941,454 A | 7/1990 | Wood et al. | |
| 4,944,443 A | 7/1990 | Oddsen et al. | |
| 4,955,882 A | 9/1990 | Hakky | |
| 4,976,710 A | 12/1990 | Mackin | |
| 4,982,726 A | 1/1991 | Taira | |
| 4,994,060 A | 2/1991 | Rink et al. | |
| 5,079,629 A * | 1/1992 | Oz | 348/77 |
| 5,131,379 A * | 7/1992 | Sewell, Jr. | 600/104 |
| 5,133,713 A | 7/1992 | Huang et al. | |
| 5,134,281 A | 7/1992 | Bryenton et al. | |
| 5,186,714 A | 2/1993 | Boudreault et al. | |
| 5,197,649 A | 3/1993 | Bessler et al. | |
| 5,201,325 A | 4/1993 | McEwen et al. | |
| 5,201,730 A | 4/1993 | Easley et al. | |
| 5,217,003 A | 6/1993 | Wilk | |
| 5,243,967 A | 9/1993 | Hibino | |
| 5,251,613 A | 10/1993 | Adair | |
| 5,258,008 A | 11/1993 | Wilk | |
| 5,305,121 A | 4/1994 | Moll | |
| 5,306,234 A | 4/1994 | Johnson | |
| 5,322,055 A | 6/1994 | Davison et al. | |
| 5,330,486 A | 7/1994 | Wilk | |
| 5,333,772 A | 8/1994 | Rothfuss et al. | |
| 5,354,266 A | 10/1994 | Snoke | |
| 5,368,015 A | 11/1994 | Wilk | |
| 5,383,880 A | 1/1995 | Hooven | |
| 5,395,030 A | 3/1995 | Kuramoto et al. | |
| 5,402,768 A | 4/1995 | Adair | |
| 5,411,508 A * | 5/1995 | Bessler et al. | 606/153 |
| 5,437,636 A | 8/1995 | Snoke et al. | |
| 5,441,507 A | 8/1995 | Wilk | |
| 5,460,182 A | 10/1995 | Goodman et al. | |
| 5,489,256 A | 2/1996 | Adair | |
| 5,496,269 A | 3/1996 | Snoke | |
| 5,518,164 A * | 5/1996 | Hooven | 227/5 |
| 3,256,875 A | 6/1996 | Tsepelev et al. | |
| 5,531,687 A | 7/1996 | Snoke et al. | |
| 5,540,711 A | 7/1996 | Kieturakis et al. | |
| 5,547,455 A * | 8/1996 | McKenna et al. | 600/113 |
| 5,603,688 A | 2/1997 | Upsher | |
| 5,604,531 A | 2/1997 | Iddan et al. | |
| 5,609,560 A | 3/1997 | Ichikawa et al. | |
| 5,630,782 A | 5/1997 | Adair | |
| 5,632,717 A * | 5/1997 | Yoon | 600/106 |
| 5,653,677 A | 8/1997 | Okada et al. | |
| 5,662,680 A | 9/1997 | Desai | |
| 5,667,473 A | 9/1997 | Finn et al. | |
| 5,667,478 A | 9/1997 | McFarlin et al. | |
| 5,667,517 A | 9/1997 | Hooven | |
| 5,797,835 A | 8/1998 | Green | |
| 5,797,944 A | 8/1998 | Nobles et al. | |
| 5,815,640 A | 9/1998 | Wang et al. | |
| 5,855,583 A | 1/1999 | Wang et al. | |
| 5,857,996 A | 1/1999 | Snoke | |
| 5,860,953 A | 1/1999 | Snoke et al. | |
| 5,865,728 A | 2/1999 | Moll et al. | |
| 5,868,760 A | 2/1999 | McGuckin, Jr. | |
| 5,878,193 A | 3/1999 | Wang et al. | |
| 5,882,331 A | 3/1999 | Sasaki | |
| 5,891,013 A * | 4/1999 | Thompson | 600/104 |
| 5,907,664 A | 5/1999 | Wang et al. | |
| 5,910,152 A | 6/1999 | Bays | |
| 5,920,390 A | 7/1999 | Farahi et al. | |
| 5,925,064 A * | 7/1999 | Meyers et al. | 606/205 |
| 5,928,137 A * | 7/1999 | Green | 600/160 |
| 5,935,143 A | 8/1999 | Hood | |
| 5,937,212 A * | 8/1999 | Kurahashi et al. | 396/20 |
| 5,941,818 A | 8/1999 | Hori et al. | |
| 5,954,634 A | 9/1999 | Igarashi | |
| 5,954,642 A | 9/1999 | Johnson et al. | |
| 5,968,060 A | 10/1999 | Kellogg | |
| 5,989,184 A | 11/1999 | Blair | |
| 5,989,274 A | 11/1999 | Davison et al. | |
| 5,993,378 A | 11/1999 | Lemelson | |
| 5,995,645 A | 11/1999 | Soenksen et al. | |
| 6,015,969 A | 1/2000 | Nathel et al. | |
| 6,019,719 A | 2/2000 | Schulz et al. | |
| 6,027,515 A | 2/2000 | Cimino | |
| 6,056,735 A | 5/2000 | Okada et al. | |
| 6,059,719 A * | 5/2000 | Yamamoto et al. | 600/127 |
| 6,063,095 A | 5/2000 | Wang et al. | |
| 6,066,090 A | 5/2000 | Yoon | |
| 6,068,627 A | 5/2000 | Orszulak et al. | |
| 6,068,647 A | 5/2000 | Witt et al. | |
| 6,069,689 A | 5/2000 | Zeng et al. | |
| 6,074,402 A | 6/2000 | Peifer et al. | |
| 6,077,285 A | 6/2000 | Boukhny | |
| 6,083,191 A | 7/2000 | Rose | |
| 6,086,528 A * | 7/2000 | Adair | 600/104 |
| 6,095,970 A * | 8/2000 | Hidaka et al. | 600/110 |
| 6,099,466 A | 8/2000 | Sano et al. | |
| 6,099,537 A | 8/2000 | Sugai et al. | |
| 6,117,152 A | 9/2000 | Huitema | |
| 6,124,597 A | 9/2000 | Shehada et al. | |
| 6,126,591 A | 10/2000 | McGarry et al. | |
| 6,134,003 A | 10/2000 | Tearney et al. | |
| 6,139,561 A | 10/2000 | Shibata et al. | |
| 6,142,930 A | 11/2000 | Ito et al. | |
| 6,159,225 A | 12/2000 | Makower | |
| 6,163,378 A | 12/2000 | Khoury | |
| 6,208,749 B1 | 3/2001 | Gutkowicz-Krusin et al. | |
| 6,208,887 B1 | 3/2001 | Clarke | |
| 6,211,904 B1 | 4/2001 | Adair et al. | |
| 6,215,550 B1 | 4/2001 | Baer et al. | |
| 6,224,227 B1 | 5/2001 | Klootz | |
| 6,236,502 B1 | 5/2001 | Kitajima | |
| 6,238,386 B1 | 5/2001 | Muller et al. | |
| 6,240,305 B1 | 5/2001 | Tsuchiya | |
| 6,244,809 B1 | 6/2001 | Wang et al. | |
| 6,245,058 B1 | 6/2001 | Suzuki | |
| 6,251,101 B1 | 6/2001 | Glockler | |
| 6,263,227 B1 | 7/2001 | Boggett et al. | |
| 6,302,311 B1 * | 10/2001 | Adams et al. | 227/176.1 |
| 6,306,082 B1 * | 10/2001 | Takahashi et al. | 600/173 |
| 6,309,345 B1 * | 10/2001 | Stelzer et al. | 600/106 |
| 6,319,199 B1 | 11/2001 | Sheehan et al. | |
| 6,331,181 B1 | 12/2001 | Tierney et al. | |
| 6,364,888 B1 | 4/2002 | Niemeyer et al. | |
| 6,387,043 B1 * | 5/2002 | Yoon | 600/109 |
| 6,398,726 B1 | 6/2002 | Ramans et al. | |
| 6,428,180 B1 * | 8/2002 | Karram et al. | 362/119 |
| 6,428,468 B1 * | 8/2002 | Knighton et al. | 600/36 |
| 6,447,444 B1 | 9/2002 | Avni et al. | |
| 6,459,822 B1 | 10/2002 | Hathaway et al. | |
| 6,471,637 B1 | 10/2002 | Chatenever et al. | |
| 6,517,479 B1 * | 2/2003 | Sekiya et al. | 600/166 |
| 6,535,764 B2 | 3/2003 | Imran et al. | |
| 6,796,939 B1 * | 9/2004 | Hirata et al. | 600/179 |
| 2001/0000672 A1 | 5/2001 | Yamakita et al. | |
| 2001/0001812 A1 | 5/2001 | Valley et al. | |
| 2001/0016725 A1 | 8/2001 | Valley et al. | |
| 2002/0026094 A1 | 2/2002 | Roth | |
| 2002/0032451 A1 | 3/2002 | Tierney et al. | |
| 2002/0032452 A1 | 3/2002 | Tierney et al. | |
| 2002/0042562 A1 * | 4/2002 | Meron et al. | 600/361 |
| 2002/0042620 A1 | 4/2002 | Julian et al. | |
| 2002/0049367 A1 * | 4/2002 | Irion et al. | 600/173 |
| 2002/0049454 A1 | 4/2002 | Whitman et al. | |
| 2002/0055795 A1 | 5/2002 | Niemeyer et al. | |
| 2002/0092533 A1 | 7/2002 | Boyd et al. | |
| 2002/0159529 A1 | 10/2002 | Wang et al. | |
| 2002/0165444 A1 | 11/2002 | Whitman | |
| 2003/0078476 A1 | 4/2003 | Hill | |
| 2003/0125788 A1 * | 7/2003 | Long | 607/133 |

| | | | |
|---|---|---|---|
| 2003/0167000 A1* | 9/2003 | Mullick et al. | 600/424 |
| 2003/0220542 A1* | 11/2003 | Belson et al. | 600/109 |
| 2004/0030382 A1 | 2/2004 | St. Goar et al. | |
| 2004/0039442 A1 | 2/2004 | St. Goar et al. | |

FOREIGN PATENT DOCUMENTS

| | | |
|---|---|---|
| DE | 2 291 980 | 2/1996 |
| DE | 196 26 433 | 1/1998 |
| EP | 0 341 719 | 11/1989 |
| EP | 0 667 115 | 8/1995 |
| EP | 0 774 231 | 5/1997 |
| GB | 2128881 | 5/1984 |
| GB | 2291980 | 2/1996 |
| JP | 53-51782 | 5/1978 |
| JP | 59 223 079 | 12/1984 |
| JP | 5-154094 | 6/1993 |
| JP | 8-502905 | 4/1996 |
| JP | 2966723 | 8/1999 |
| WO | WO 82/03545 | 10/1982 |
| WO | WO 83/00992 | 3/1983 |
| WO | WO 92/16141 | 10/1992 |
| WO | WO93/15648 * | 8/1993 |
| WO | WO 94/05200 A1 | 3/1994 |
| WO | WO 96/27991 * | 9/1996 |
| WO | WO 98/32380 | 7/1998 |
| WO | WO 99/26411 * | 5/1999 |
| WO | WO 99/30610 | 6/1999 |
| WO | WO 99/32028 | 7/1999 |
| WO | WO 00/22975 | 4/2000 |
| WO | WO 00/76391 | 12/2000 |
| WO | WO 01/10291 | 2/2001 |
| WO | WO 01/35813 | 5/2001 |
| WO | WO 01/056460 | 8/2001 |
| WO | WO 01/62163 | 8/2001 |
| WO | WO 02/055126 | 7/2002 |

OTHER PUBLICATIONS

"Manometric Findings in Dysphagia Secondary to Left Atrial Dilatation Digestive Diseases and Sciences", vol. 36, May 1991, M. Cappell.

"Case Report: Late Pulmonary Embolization . . . ", Apr. 1985, E.D. Mayer et al.

"Fiberoptic examination of the inferior vena cava . . . ", Thorac. Cardiovascular Surgeon, 33, Jun. 1990, A. R. Hartman.

"Media Stinoscope: Another Use." Journal of Cardio Surgery, 27, Mar. 1986, P. R. Behl.

"Special Pacemaker Catheter Techniques: The Transmediastinal Placement of Sensing Electrodes", Apr. 1976, Kleinert et al.

"Endobronchial Resection with the ND-Yag Laser—Two Year Experience in an Australian Unit", Australia/New Zealnd Journal of Medicine, Apr. 1990, R. J. Pierce.

"Cardiovascular Fiberoptic Endoscopy: Development and Clinical Application", Apr. 1980, T. Tanabe et al.

European Search Report for EP 11 00 1302 dated May 4, 2011.

* cited by examiner

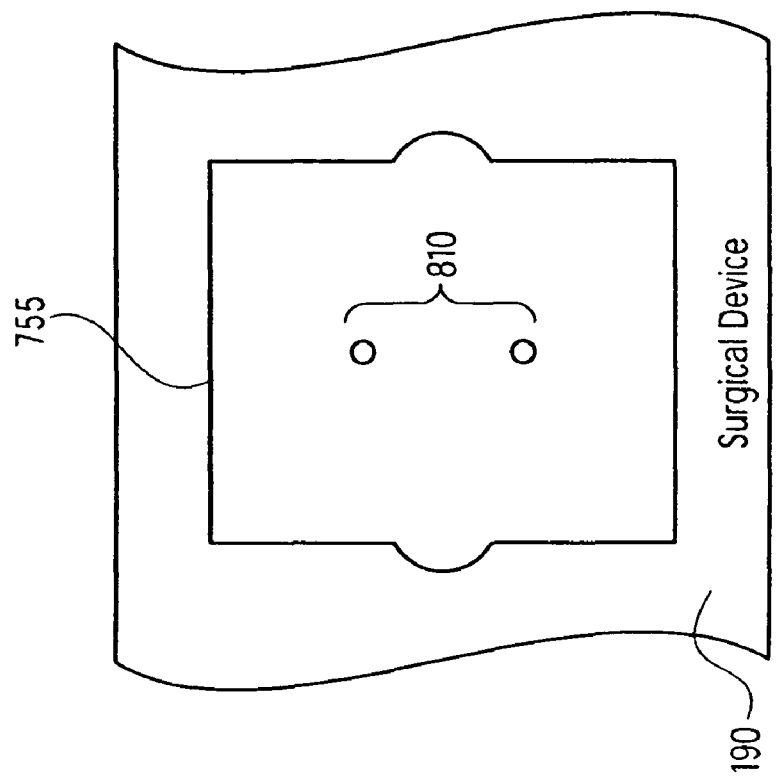
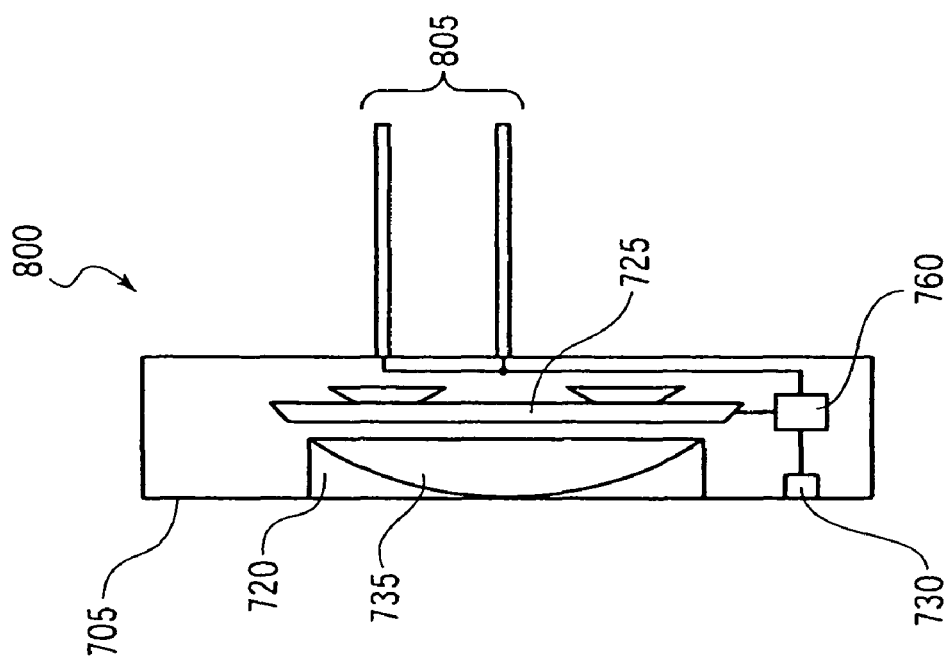
Fig. 8b
Fig. 8a

IMAGING DEVICE FOR USE WITH A SURGICAL DEVICE

CROSS-REFERENCE TO RELATED APPLICATIONS

This application incorporates each of U.S. patent application Ser. No. 09/324,452, filed on Jun. 2, 1999, U.S. application Ser. No. 09/723,715, filed on Nov. 28, 2000, U.S. application Ser. No. 09/324,451, filed on Jun. 2, 1999, U.S. application Ser. No. 09/351,534, filed on Jul. 12, 1999, U.S. application Ser. No. 09/510,923, filed on Feb. 22, 2000, U.S. application Ser. No. 09/510,927, filed on Feb. 22, 2000, U.S. application Ser. No. 09/510,932, filed on Feb. 22, 2000, and U.S. application Ser. No. 09/836,781, filed on Apr. 17, 2001, and U.S. patent application Ser. No. 09/887,789, filed on Jul. 22, 2001, in its entirety by reference. This application also claims the benefit of each of U.S. Patent Application Ser. No. 60/285,193, filed on Apr. 20, 2001, U.S. Patent Application Ser. No. 60/300,107, filed on Jun. 22, 2001, and U.S. Patent Application Ser. No. 60/344,648, filed on Dec. 31, 2001, each of which is expressly incorporated herein in its entirety by reference.

FIELD OF THE INVENTION

The present invention relates to an imaging device which may be used in conjunction with a surgical device.

BACKGROUND INFORMATION

Surgeons utilize various surgical instruments for inter-abdominal, inter-thoracic and other similar surgical procedures. Typically, surgeons desire to perform these procedures using minimally invasive surgical techniques. In an endoscopic procedure, for example, a small incision is made in a patient and an endoscope is inserted therein in order to view the body cavity in which the surgeon intends to perform the surgery. These types of surgical procedures typically require the use of an endoscope which enables the surgeon to obtain a view of the body cavity and the manipulation of a surgical device used during the surgery. Many times, the surgeon inserts both the endoscope and the surgical device either through the same incision or may use separate incisions for each device. In most surgical procedures using an endoscope, a member of the surgical team may continuously monitor the positioning of the endoscope in order maintain a suitable view of the body cavity and the manipulation of the surgical device.

In addition to the use of an endoscope, some surgical devices include an arrangement to indicate the position of the components while in use. A remote status indicator may provide this information to the user via a LCD indicator which is coupled to an electromagnetic sensor. In one exemplary embodiment, a surgical instrument may include an anvil portion and a staple, blade and reservoir (SBR) portion. The surgical instrument detachably couples to an electro-mechanical driver device via a shaft. The surgeon advances the shaft and the SBR portion of the attachment into the body cavity. The base of the anvil portion and the outer edge of the SBR housing may include an electromagnetic sensor which is coupled to the LCD indicator of the handle, thereby permitting the surgeon to know the position of the anvil and the SBR during the surgical procedure.

Although the use of the LCD indicator, as described above, provides the surgeon with some information regarding the position of the surgical instruments, such an LCD indicator may be used in conjunction with an endoscope. By using the endoscope and additionally the LCD indicator, the surgeon may receive visual images of the body cavity (via the endoscope) and an indication of the position of the surgical instrument during the surgery (via the LCD indicator). It would be advantageous to provide an imaging device that couples to a surgical instrument itself. Such an imaging device may provide a surgeon with both images of the body cavity and the manipulation of the surgical instrument during the procedure. It would also be advantageous to provide an imaging device which is reusable on various surgical instruments that are adapted to receive it.

SUMMARY

In one embodiment according to the present invention, an imaging unit is provided, including a housing configured to detachably couple to an outer surface of a surgical device, and an image capture arrangement configured to generate image data; the imaging unit may also include a circuit arrangement disposed within the housing and electrically coupled to the image capture arrangement, in which the circuit arrangement is configured to communicate the image data to at least one remote device.

In another embodiment according to the present invention, a surgical attachment is provided, including a surgical device, and an imaging unit having a housing configured to detachably couple to an outer surface of the surgical device and an image capture arrangement configured to generate image data; the imaging unit may further include a circuit arrangement disposed within the housing and electrically coupled to the image capture arrangement, in which the circuit arrangement is configured to communicate the image data to at least one remote device.

In another embodiment according to the present invention, a surgical system is provided, including an electro-mechanical driver device, a surgical device detachably coupled to the electro-mechanical driver device, and an imaging unit having a housing configured to couple to an outer surface of the surgical device and an image capture arrangement configured to generate image data; the imaging unit may further include a circuit arrangement disposed within the housing and electrically coupled to the image capture arrangement, in which the circuit arrangement is configured to communicate the image data to at least one remote device.

BRIEF DESCRIPTION OF THE DRAWINGS

FIG. 4b is a side view of the image capture arrangement illustrated in FIG. 4a.

FIG. 8a illustrates another exemplary imaging pod according to the present invention.

FIG. 8b illustrates an exemplary receptacle of a surgical device configured to receive the imaging pod illustrated in FIG. 8a.

DETAILED DESCRIPTION

Figure 1:
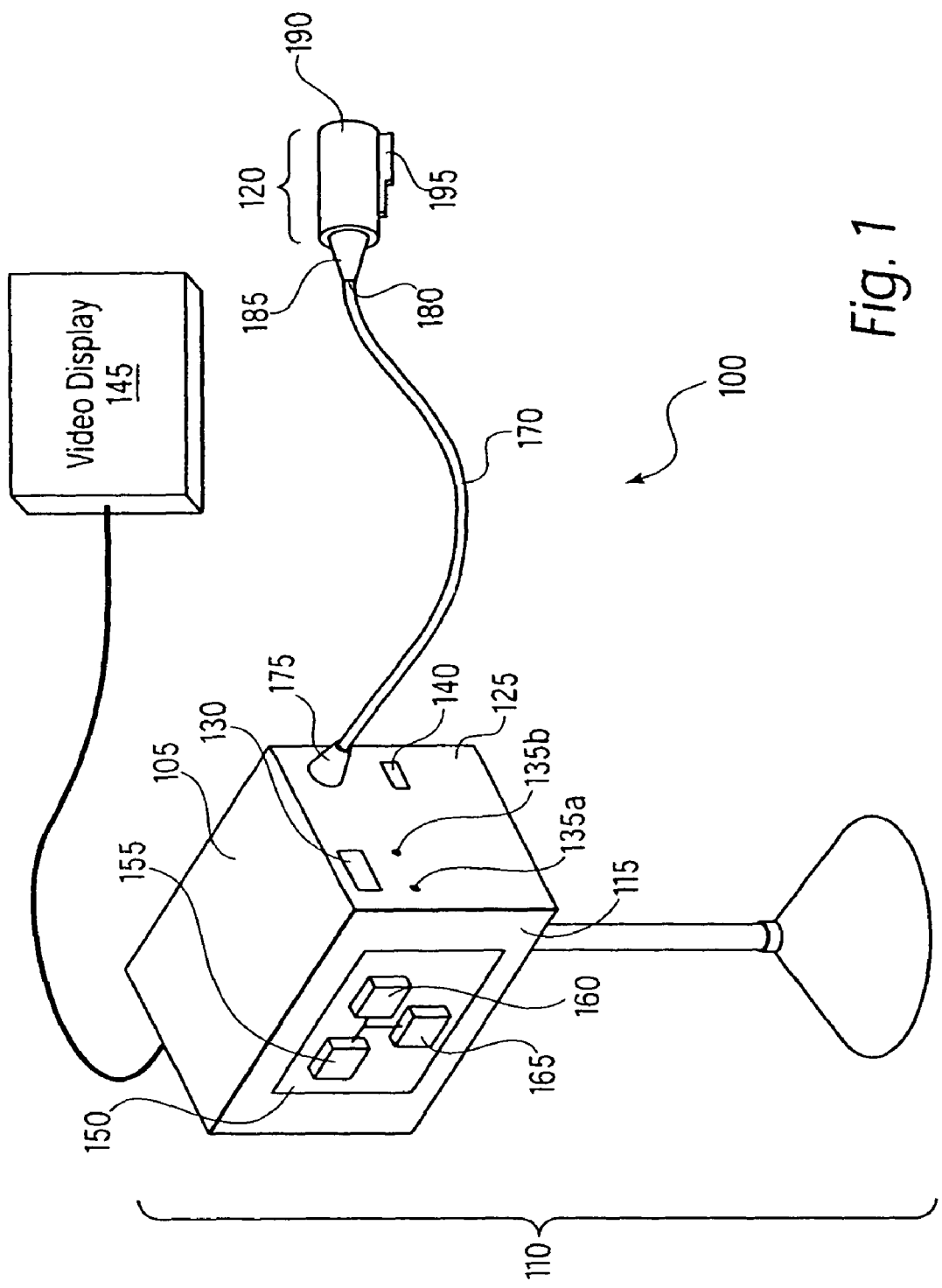
FIG. 1 illustrates an exemplary surgical system 100 according to the present invention.

Referring now to FIG. 1, there is seen a surgical system 100. Surgical system 100 includes an electro-mechanical driver device 110 detachably coupled to a surgical attachment 120. Such an electro-mechanical driver device is described in, for example, U.S. patent application Ser. No. 09/723,715, entitled "Electro-Mechanical Surgical Device," U.S. patent application Ser. No. 09/836,781, entitled "Electro-Mechanical Surgical Device, filed on Apr. 17, 2001, and U.S. patent application Ser. No. 09/887,789, entitled "Electro-Mechanical Surgical Device," filed on Jun. 22, 2001, each of which is expressly incorporated herein in its entirety by reference. Electro-mechanical driver device 110 may include, for example, a remote power console (RPC) 105, which includes a housing 115 having a front panel 125. Mounted on front panel 125 are a display device 130 and indicators 135a, 135b. A connection slot 140 is also provided on front panel 125. Electro-mechanical driver device 110 may also include a video display 145, e.g., a television monitor, computer monitor, CRT or other viewing device, attached to the RPC 105. Video display 145 may receive, for example, image signals (e.g., video signals) from an imaging device 195. The electro-mechanical driver device 110 may also include a reception system 150 having a receiver or transceiver 155 and circuitry 160 operable to convert signals received from the imaging device 195 into a form suitable for display on video display 145. The reception system 150 may also include a memory device 165 for buffering and/or storing processed image data received from the imaging device 195.

A flexible shaft 170 may extend from housing 115 and may be detachably secured thereto via a first coupling 175. The distal end 180 of flexible shaft 170 may include a second coupling 185 adapted to detachably secure the surgical attachment 120 to the distal end 180 of the flexible shaft 170.

Disposed within the interior channel of the flexible shaft 170, and extending along the length thereof, may be rotatable shafts, steering cables, one or more data transfer cables and power transfer leads, all of which terminate at the second coupling 185 at the distal end 180 of the flexible shaft 170. The electro-mechanical driver device 110 may include a motor system (not shown), which includes one or more motors configured to rotate the drive shafts and to apply tension or otherwise drive the steering cables to thereby steer the distal end 180 of the flexible shaft 170.

Figure 2A:
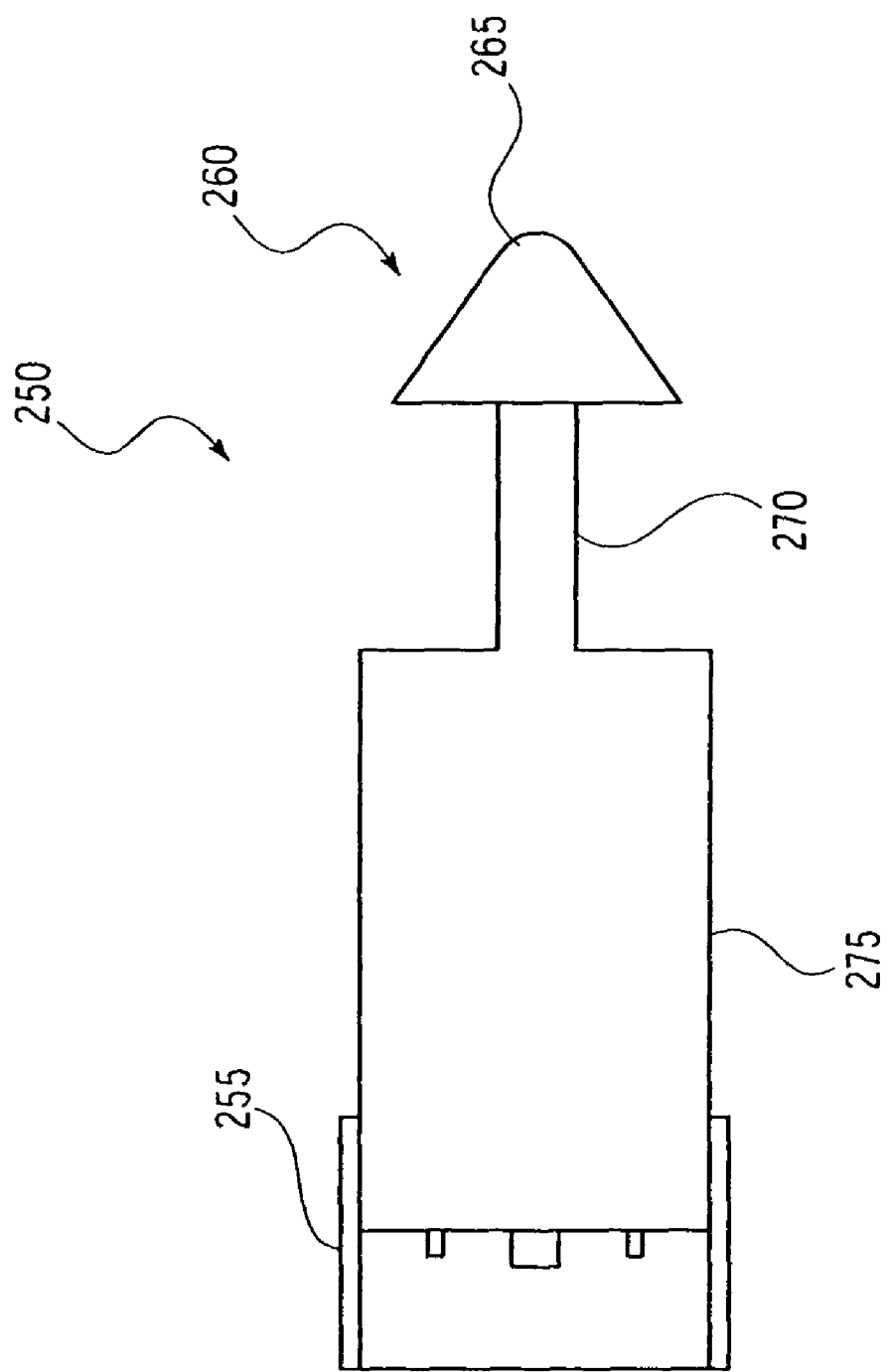
FIG. 2a illustrates a circular surgical stapler attachment.

Various types of surgical devices 190 may be attached to the distal end 180 of the flexible shaft 170, such as a circular surgical stapler attachment (CSS) 250, shown schematically in FIG. 2a. The CSS 250 includes a coupling 255 adapted by size and configuration to cooperate with the second coupling 185 of flexible shaft 170 to detachably couple the CSS 250 thereto. CSS 250 includes an anvil portion 260 having an anvil 265 mounted on the distal end of an anvil stem 270. The anvil stem 270 is extended and retracted by the operation of an anvil drive shaft (not shown), which is rotatably secured within the body portion 275 of the CSS 250. CSS 250 further includes a staple driver/cutter mechanism (not shown) within the body portion 275. In operation, the extension and refraction of the anvil 265 and the staple driver/cutter may be effected by the operation of motors within the electro-mechanical driver device 110. Movement and control of the anvil 265 and staple driver/cutter may be performed through the use of a remote control unit (not shown). The position and location of the anvil 265 and staple driver/cutter are indicated by signals transmitted to the electro-mechanical driver device 110 and displayed for the user on the display device 130 and indicators 135a, 135b. CSS 250 further includes a data connector (not shown) adapted to electrically and communicatively couple to second coupling 185.

Figure 2B:
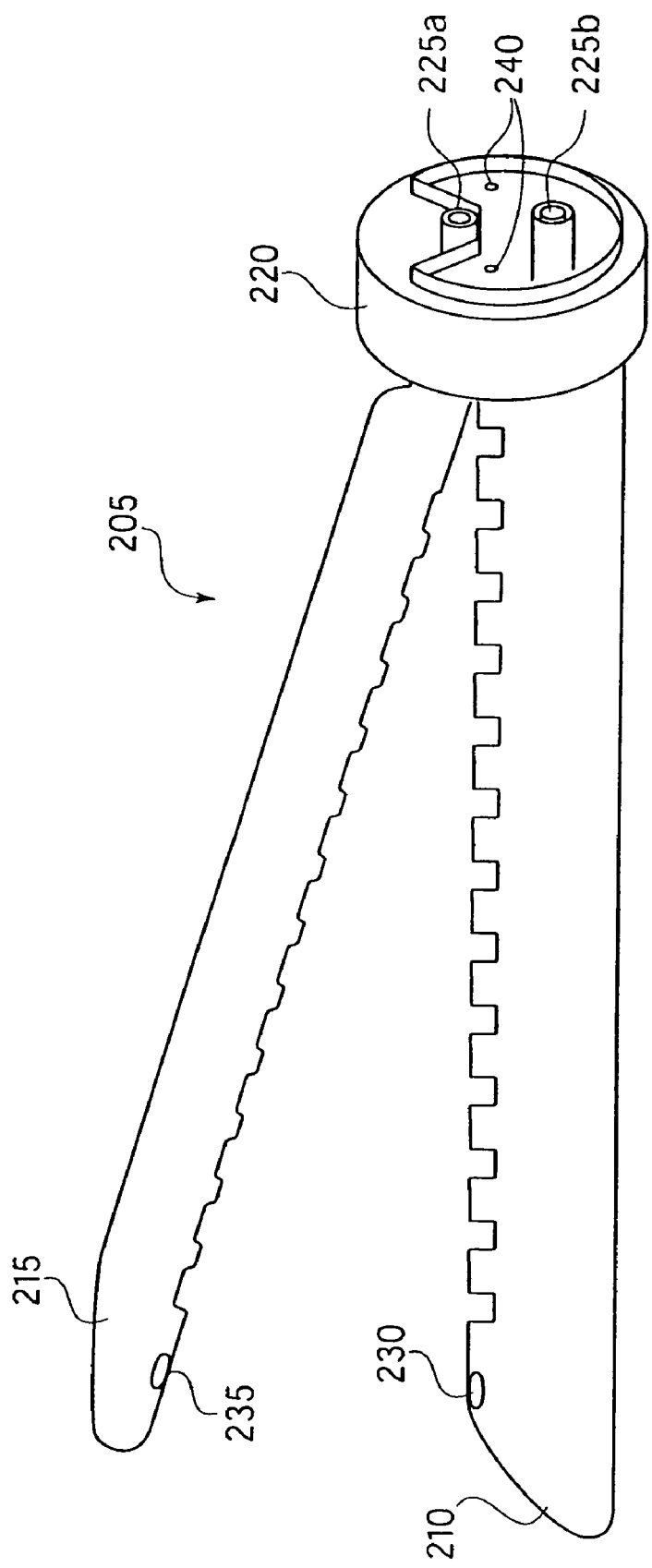
FIG. 2b illustrates a linear surgical stapler.

Referring now to FIG. 2b, there is seen another exemplary surgical device 190 as a linear surgical stapler 205, such as described in detail in U.S. patent application Ser. No. 09/324,452 which is expressly incorporated herein by reference in its entirety. The linear surgical stapler 205 may include a separating jaw system comprising a lower jaw 210, an upper jaw 215 and a coupling 220. Coupling 220 may include two hexagonal shaped sockets 225a, 225b into which second coupling 185 of flexible shaft 170 is detachably received. At the distal tip of the upper jaw 215 and lower jaw 210 may be situated two opposing magnetic sensors 230, 235, each coupled to a circuit component (not shown) which connects to the electro-mechanical driver device 110 via flexible shaft 170. When the lower and upper jaws 210, 215 come together, the circuit is closed and indicators 135a, 135b of the electro-mechanical driver device 110 provide a signal indicating that the stapling mechanism (not shown) of lower jaw 210 may be safely fired. The linear surgical stapler 205 may also include a shaft and driver component configured to close jaws 210, 215 onto tissue and to drive staples into the tissue for closure. The magnetic sensors 230, 235 and circuitry associated with the linear surgical stapler attachment 205 may also, for example, provide a user with an indication when a section of tissue has been fully clamped.

The linear surgical stapler 205 may also include electrodes (not shown). The electrodes may receive RF energy through contacts 240 and enable the coagulation and/or anastomosing of tissue. The linear surgical stapler attachment 205 may incorporate various electrode and/or stapling configurations, as described in U.S. Patent Application Ser. No. 60/285,113, entitled "A Surgical Linear Clamping, Stapling, and Cutting Device", filed on Apr. 20, 2001 and U.S. Patent Application Ser. No. 60/289,370, entitled "Bipolar Surgical Device" filed on May 8, 2001, each of which is expressly incorporated herein by reference in its entirety.

Although FIG. 2a, 2b show only a circular surgical stapler and a linear surgical stapler, respectively, it should be appreciated that the surgical device 190 may include other arrangements. For example, surgical device 190 may include a trocar device, as described in U.S. patent application Ser. No. 10/098,217, filed on Mar. 14, 2002, which is expressly incorporated herein by reference.

Figure 3A:
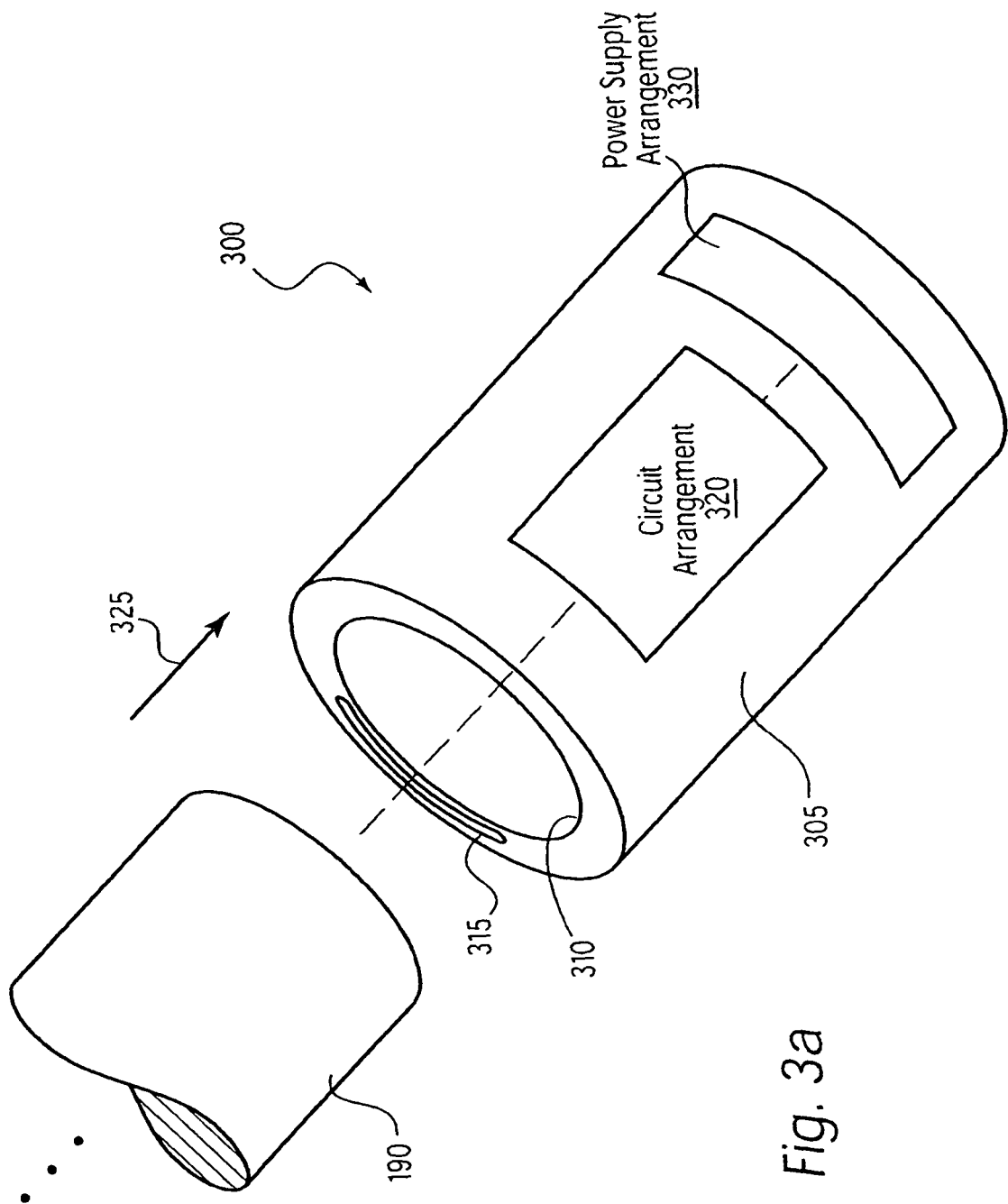
FIG. 3a illustrates a first exemplary imaging device according to the present invention configured to couple to a surgical device.

Referring now to FIG. 3a, there is seen a first exemplary imaging device 300 configured to couple to the surgical device 190, for example, a linear stapler or a circular surgical stapler. Imaging device 300 includes a housing 305 having a bore 310, an image capture arrangement 315 (e.g., a camera), a circuit arrangement 320 electrically coupled to the image capture arrangement 315, and a power supply arrangement 330 for supplying power to the imaging device 300.

Figure 3B:
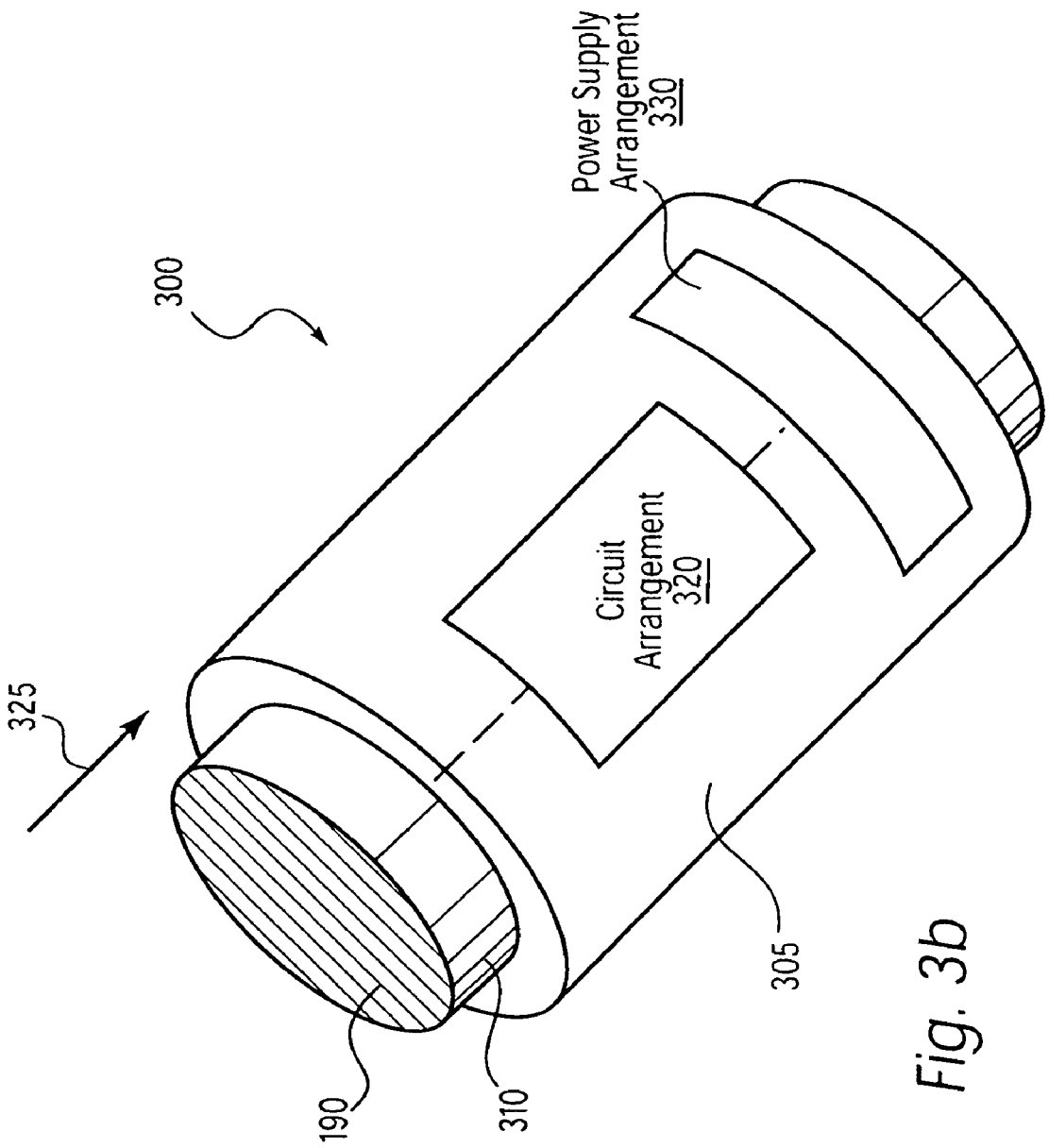
FIG. 3b illustrates the imaging device of FIG. 3a, with the surgical device coupled to the imaging device.

The imaging device 300 is suitably configured to slidably receive the surgical device 190 within bore 310. For this purpose, the surgical device 190 may be inserted into the bore 310 in a first direction 325, as shown in FIG. 3b. Once inserted, a coupling mechanism (not shown) may hold the surgical device 190 in place within the bore 310.

It should be appreciated that the coupling mechanism may include any arrangement suitable for detachably holding the surgical device 190 in place within the bore 310, such as, clamps, nuts, bolts, clasps, straps, a frictional-fit arrangement, a snap-fit arrangement, etc. Thus, the imaging device 300 may be detachably coupled to or mounted on an outer surface of the surgical device 190. Configured in this manner, after the imaging device 300 is used with the surgical device 190, the imaging device 300 may be removed from the surgical device 190 and reused on another surgical device. This may be particularly advantageous if, for example, the surgical devices are disposable with and it is desired to reuse the imaging device 300 several times. Of course, in an alternate embodiment, the surgical device 190 may be permanently coupled to the imaging device 300.

Although FIGS. 3a, 3b show bore 310 having a cylindrical shape, it should be appreciated that bore 310 may be suitably shaped and configured to provide compatible attachment to other surgical devices, which may or may not be cylindrical in shape.

Figure 4A:
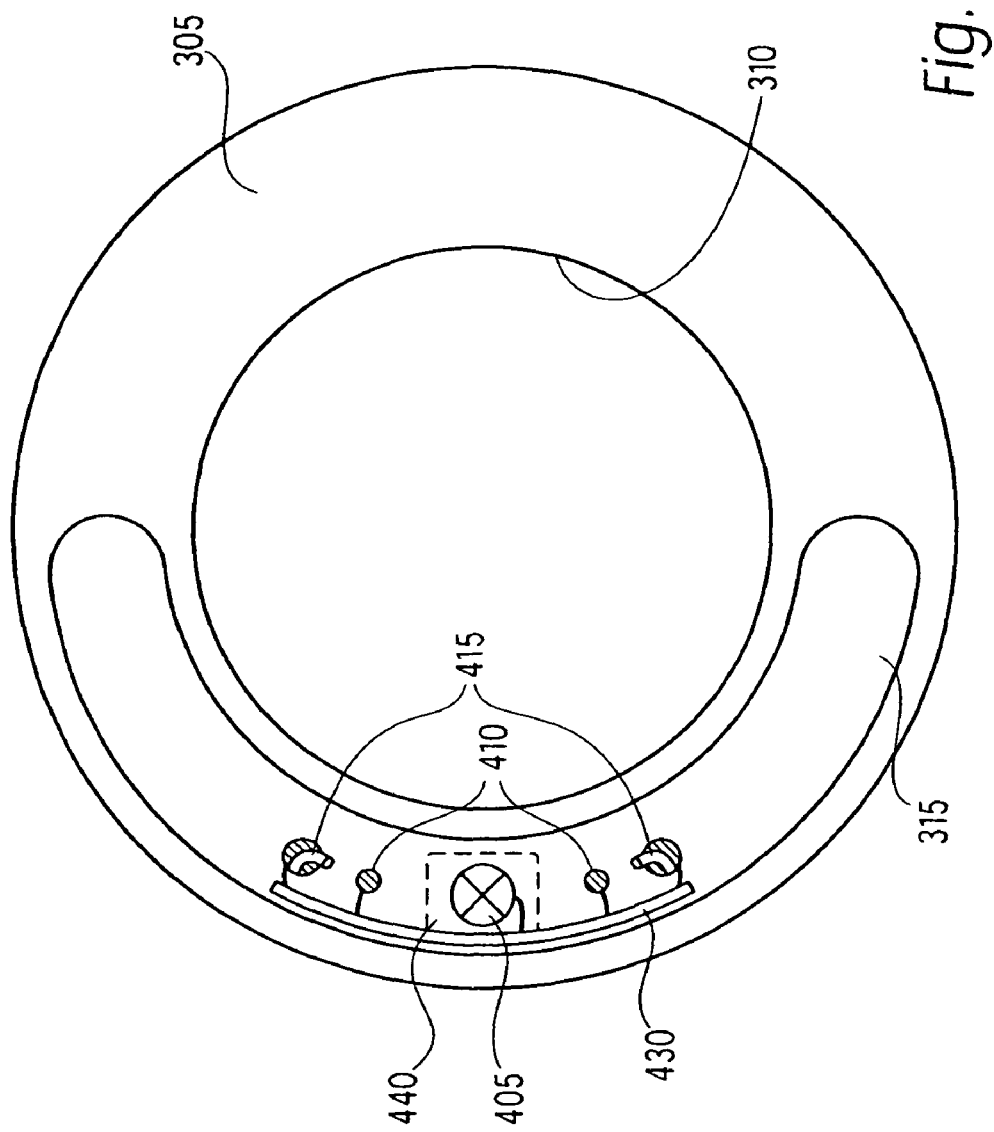
FIG. 4a illustrates an exemplary image capture arrangement according to the present invention.

Referring now to FIG. 4a, there is seen a frontal view of the image capture arrangement 315 illustrated in FIGS. 3a, 3b showing further detail. As shown in FIG. 4a, the image capture arrangement 315 includes a lens 405, a light source 410 for illuminating an object to be imaged (e.g., fiber optic light sources, light bulbs, LEDs, etc.), an image sensor 440 (e.g., a light sensitive device such as a CCD or CMOS-type image sensor) positioned to capture an image via the lens 405. In one embodiment, the image capture arrangement 315 may further include a cleaning arrangement 415 for cleaning debris from the lens 405. Each of the lens 405, the light source 410, the image sensor 440, and the cleaning arrangement 415 is communicatively coupled to data bus 430.

In operation, the image sensor 440 receives an image as seen, for example, from the distal end of the surgical device 190 via lens 405. The image capture arrangement 315 generates image data in accordance with the image and communicates the image data to the circuit arrangement 320 via data bus 430.

In the exemplary embodiment shown, the image sensor 440 is positioned behind the lens 405. However, the image sensor 440 may be arranged in a position remote from the lens 405, with light from the lens 405 being transmitted to the image sensor 440 via, for example, fiber optic connections. In one exemplary embodiment, the image sensor 440 is positioned in the housing 305. In another exemplary embodiment, the image sensor 440 is positioned in the flexible shaft 170, a coupling thereto, and/or the electro-mechanical driver device 110. In any event, image data may be transmitted to the electro-mechanical driver device via a wireless or wired connection.

Figure 4B:
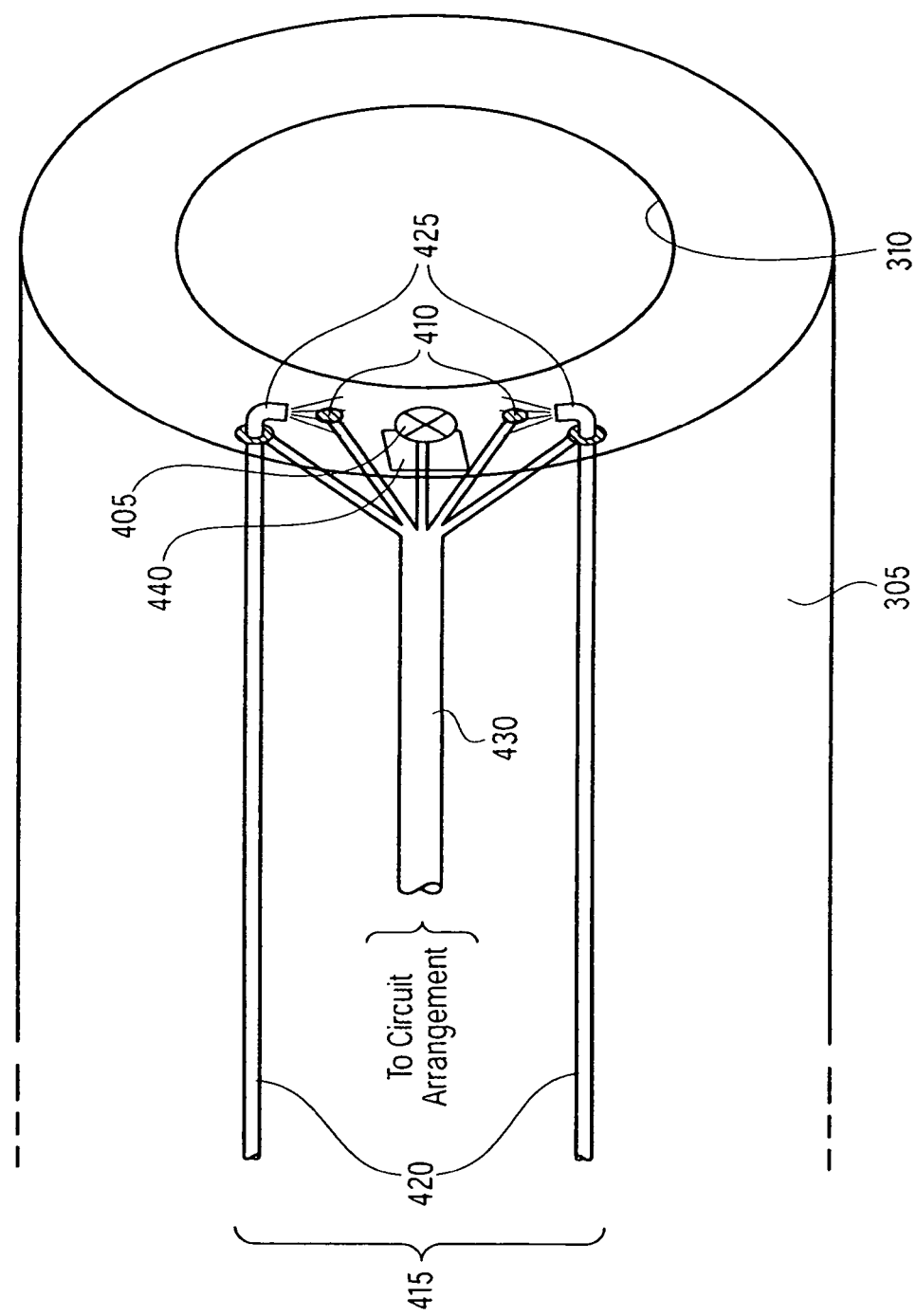

Referring now to FIG. 4b, there is a side view of the image capture arrangement 315 illustrated in FIG. 4a. The cleaning arrangement 415 may include, for example, hollow stems 420 for dispersing an air/water mixture across lens 405. For this purpose, proximal ends (not shown) of the hollow stems 420 may receive the air/water mixture from a remote source (not shown), for example, the electro-mechanical driver device 110. The air/water mixture is propelled through the hollow stems, exiting the distal ends 425 of the hollow stems 420. In this manner, the air/water mixture is dispersed across the lens 405 to help clean debris from the lens 405 during use.

In addition to communicating the image data to the circuit arrangement 320 via data bus 430, the image capture arrangement 315 receives control data from the circuit arrangement 320 via the data bus 430. The control data may, for example, control zooming of the lens 405, control the illumination produced by the light source 410, and/or control the flow rate of the air/water mixture propelled through the hollow stems 420 of the cleaning arrangement 415.

It should be appreciated that the image capture arrangement 315 may include one or more lenses 405, one or more image sensors 440, and/or one or more light sources 410. Multiple lenses 405 and/or image sensors 440 may permit a user to switch between different lenses 405 to obtain multiple views at different perspectives. For example, the user may view different images through every step of a surgical procedure. Furthermore, multiple lenses may permit panoramic or wide views.

Figure 5:
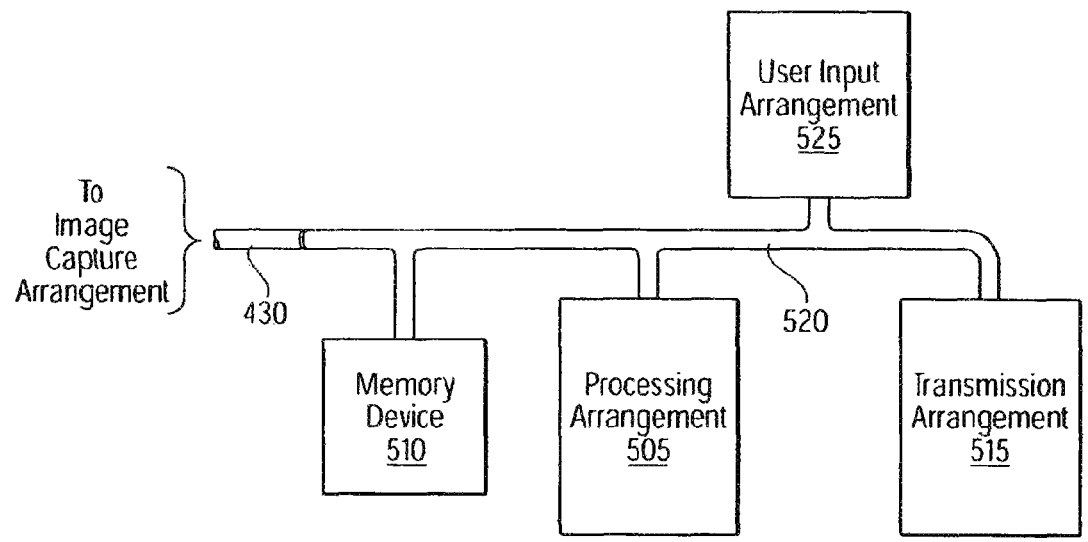
FIG. 5 illustrates an exemplary circuit arrangement according to the present invention.

Referring now to FIG. 5, there is seen further detail of the circuit arrangement 320 illustrated in FIGS. 3a, 3b. The circuit arrangement 320 includes circuitry suitable for receiving the image data from the image capture arrangement 315 and communicating the image data to a remote source, such as the electro-mechanical driver device 110. The circuitry may be physically situated, for example, on a rigid or flexible circuit board situated within the housing 305 of the imaging device 300. Circuit arrangement 320 may include a processing arrangement 505, a memory device 510, user input arrangement 525, and a transmission arrangement 515, each of which is communicatively coupled via data bus 520. The data bus 430 of the image capture arrangement 315 is also communicatively coupled to the data bus 520. In this manner, the image data may be received from the image capture arrangement 315 and communicated to the processing arrangement 505 and/or the memory device 510 via data bus 520.

The memory device 510 may include any read/writable memory device capable of storing the image data, such as RAM, FLASH, EPROM, EEPROM, etc. The image data received from the image capture arrangement 315 may be, for example, stored directly on the memory device 510 for subsequent processing by the processing arrangement 505. In this manner, the memory device 510 receives the image data from the image capture arrangement 315 and then communicate the image data to the processing arrangement 505. Alternatively, the image data may be transmitted directly to the processing arrangement 505 for processing. In this manner, the processing arrangement 505 receives the image data from the image capture arrangement 315 directly via the data bus 520. Additionally, the memory device 510 may receive and store processed image data from the processing arrangement 505 for subsequent additional processing and/or for direct transmission to the remote device via the transmission arrangement 515. Alternatively, the image data may be transmitted directly from the image capture arrangement 315 to a processor of the electro-mechanical driver device 110.

The user input arrangement 525 is configured to receive commands from a user. The commands may include, for example, commands to zoom the lens 405, to switch between different views, to receive continuous (e.g., video) or still images, to control the illumination produced by the light source 410, to control the flow rate of the air/water mixture propelled through the hollow stems 420 of the cleaning arrangement 415, to switch to panoramic view, etc.

For this purpose, the user input arrangement 520 may include, for example, a wireless receiver for receiving the commands wirelessly from a remote control unit. Alternatively, the user input arrangement 520 may include, for example, electrical contacts for communicatively coupling to the electro-mechanical driver device 110 via wires disposed within the flexible shaft 170 or external to the flexible shaft 170. In this manner, the user input arrangement 520 may receive the commands via the remote power console 105 of the electro-mechanical driver device 110.

The user input arrangement 520 generates user input data in accordance with the commands received from the user and communicates the user input data to the processing arrangement 505 via the data bus 520. The processing arrangement 505 is configured to control the image capture arrangement 315 and process the image data in accordance with the user input data received from the user input arrangement 520.

To control the image capture arrangement 315, the processing arrangement 505 may generate control data for controlling the various functions of the image capture arrangement 315 in accordance with the user input data received from the user input arrangement 520. For this purpose, the processing arrangement 505 communicates the control data to the image capture arrangement 315 via data buses 430, 520. The control data may, for example, control zooming of the lens 405, control the illumination produced by the light source 410, and/or control the flow rate of the air/water mixture propelled through the hollow stems 420 of the cleaning arrangement 415.

The processing arrangement 505 also processes the image data in accordance with the user input data received from the user input arrangement 520. In this manner, the processing arrangement 505 may process the image data to communicate continuous or still images, to perform a digital zoom, etc. In this manner, the imaging device 300 may provide a surgeon with a video image as the surgical attachment 120 is inserted and probed through, for example, the colon area of a patient. Both moving and still images may be provided to surgeon via the imaging device 300. For example, while the surgeon is probing the colon to locate cancerous tissue, the imaging device 300 may supply a continuous image of the colon. Should the surgeon encounter an image that he or she would prefer to view as a still image, the surgeon may instantaneously freeze the moving image by activating the corresponding control mechanisms. Accordingly, the freeze frame image may be manipulated as desired, i.e., rotated, zoomed and/or magnified.

The moving images may also be stored and manipulated as desired for subsequent visual analysis.

The transmission arrangement 515 receives the processed image data from the processing arrangement 505 via the data bus 520 and communicates the processed image data to the remote device (not shown). For this purpose, the transmission arrangement 515 may include a wireless transmitter operable to convert the processed image data into an RF transmission to be wirelessly received by the remote device. Alternatively, the transmission arrangement 515 may include, for example, electrical contacts for communicatively coupling to the electro-mechanical driver device 110 via wires disposed within or external to the flexible shaft 170. In this manner, the transmission arrangement 515 may communicate the processed image data to the video display 145 of the electro-mechanical driver device 110.

Figure 6:
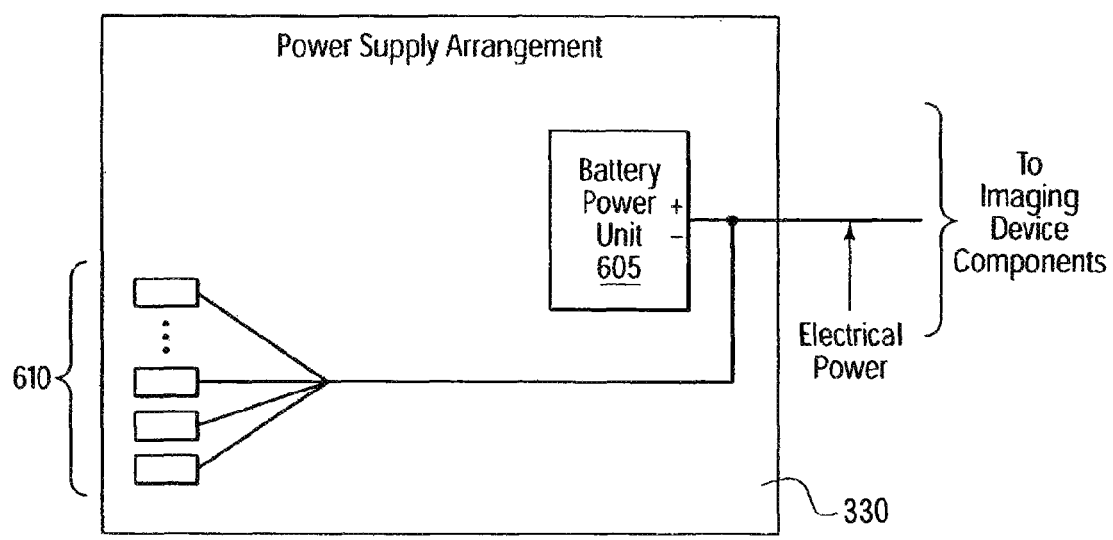
FIG. 6 illustrates an exemplary power supply arrangement according to the present invention for providing electrical power to an imaging device.

Referring now to FIG. 6, there is seen further detail of the exemplary power supply arrangement 330 illustrated in FIGS. 3a, 3b. Power supply arrangement 330 includes a battery power unit 605 for providing electrical power to the imaging device 300. The battery power unit 605 may include, for example, nickel cadmium batteries, nickel metal-hydride batteries, lithium batteries, etc. In addition to or in lieu of the battery power unit 605, power supply arrangement 330 may include power contacts 610 for receiving electrical power from an external source (not shown), for example, the electro-mechanical driver device 110. In this manner, the electro-mechanical driver device 110 may transmit the electrical power to the power supply arrangement 330 via wires disposed within or external to the flexible shaft 170.

The battery power unit 605 may be configured, for example, to provide electrical power to the imaging device 300 if the power contacts 610 are not receiving electrical power from the external source, for example, from the electro-mechanical driver device 110. In this manner, the battery power unit 605 may function as a "battery-backup," to ensure that the imaging device 300 receives electrical power in the event power transmission from the external source is interrupted and/or removed.

Figure 7A:
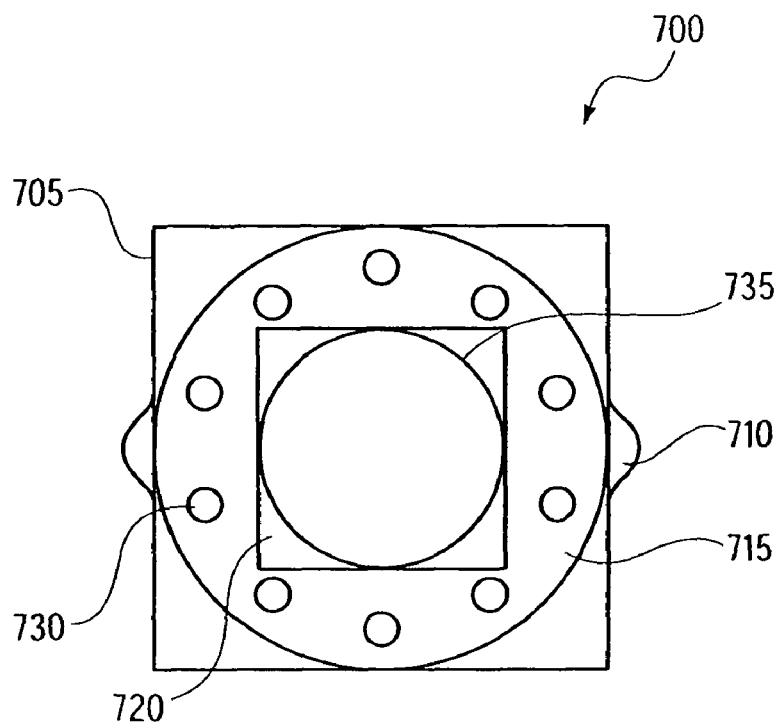
FIG. 7a illustrates another exemplary imaging device in the form of an imaging pod.

Referring now to FIG. 7a, there is seen another exemplary imaging device in the form of imaging pod 700. The imaging pod 700 includes a housing 705 having an attachment arrangement 710 and an image capture arrangement 715 situated within the housing. The image capture arrangement 715 includes one or more light sources 730 and an optical system 720 with a focusing lens 735. The attachment arrangement 710 may include, for example, pins, spring loaded bearings, ridges, etc. configured to detachably couple the imaging pod 700 to a corresponding receptacle of the surgical device 190. The housing 705 may be formed of, for example, a transparent plastic material, although the housing may be formed of other materials as well.

Figure 7B:
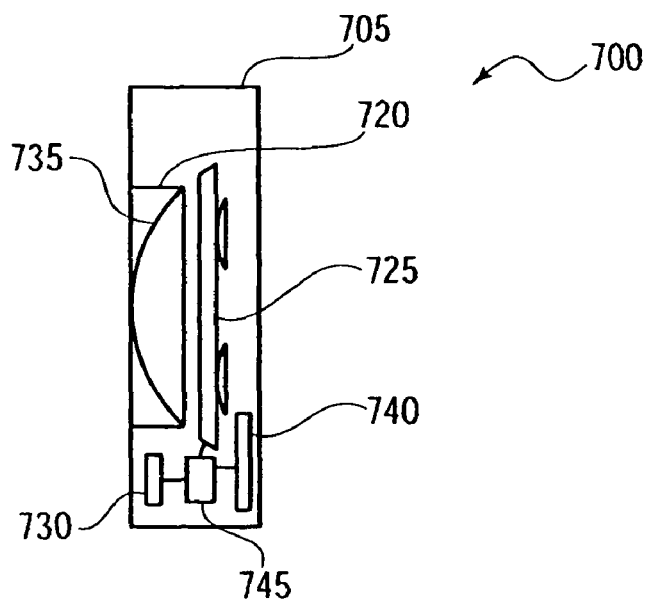
FIG. 7b is a side view of the imaging device illustrated in FIG. 7a showing further detail.

Referring now to FIG. 7b, there is seen further detail of imaging pod 700 illustrated in FIG. 7a. As seen in FIG. 7b, the image capture arrangement 715 further includes an imaging sensor, e.g., a light sensitive device such as a charged coupled device (CCD) 725. As the imaging pod is directed toward an object to be imaged, the focusing lens 735 focuses reflected light onto CCD 725. A wireless transmitter (or, e.g., a transceiver) 740 is situated in the housing 705 and communicatively coupled to the CCD 725. An example of such a wireless transmitter is described in U.S. Pat. No. 5,604,531, expressly incorporated herein by reference in its entirely. Additionally, a power source 745, such as a small battery, is situated in the housing 705 and operable to provide electrical power to the CCD 725, light sources 730, and the wireless transmitter 740. In operation, images captured by CCD 725 may be wirelessly transmitted via wireless transmitter 740 to a corresponding receiver (or transceiver) in a remote device, such as the electro-mechanical driver device 110.

Although, the present embodiment is described as using a CCD as an image sensor, other suitable image sensors may also be used, such as a CMOS (Complementary Metal Oxide Semiconductor) type image sensor. The CMOS sensor may require less power than a CCD image sensor, due to its greater sensitivity to light. A CMOS image sensor may include, for example, a photo diode and/or a photo transistor to detect reflected light from an object to be imaged. The CMOS image sensor may transmit the image data as an analog signal or, alternatively, as a digital signal after processing by an analog-digital converter.

Figure 7C:
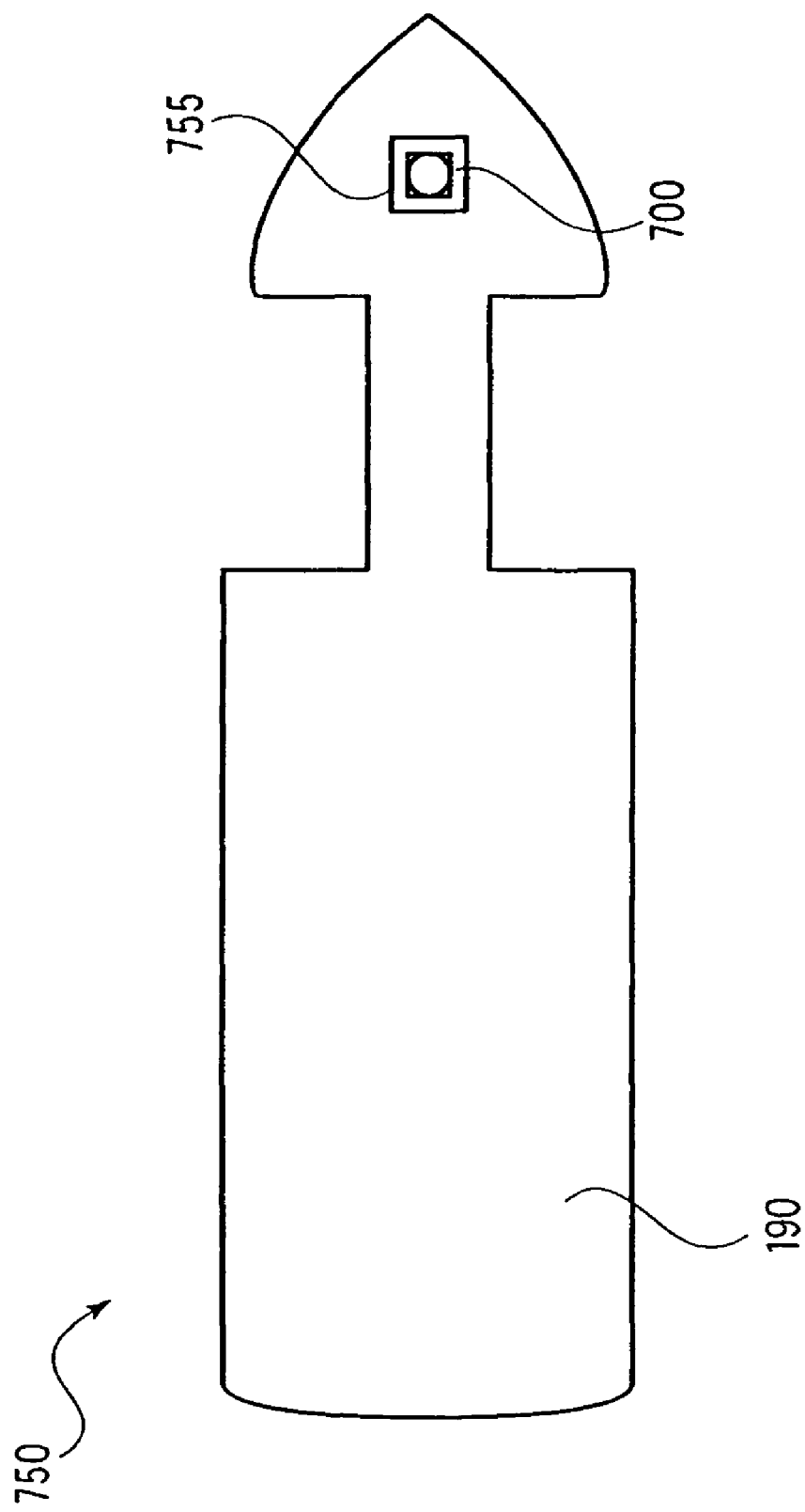
FIG. 7c illustrates a surgical attachment with an imaging pod coupled to a surgical device.

Referring now to FIG. 7c, there is seen a surgical attachment 750 including the imaging pod 700 coupled to surgical device 190. The imaging pod 700 is detachably received within a receptacle 755 of the surgical device 190. Accordingly, if the surgical device 190 is designed as a disposable unit, the imaging pod 700 may be removed from the surgical device 190 and reused in connection with another surgical device. Alternatively, the imaging pod 700 may be permanently secured to, or even integral with, the surgical device 190. In this regard, the permanently coupled imaging pod 700 would be disposed along with the surgical device 190.

Referring now to FIG. 8a, there is seen another exemplary imaging pod 800. Imaging pod 800 is similar to the imaging pod 700 described in connection with FIGS. 7a, 7b, 7c, except that imaging pod 800 includes wired connections for transmitting the image data to the remote device, such as the electro-mechanical driver device 110. As shown in FIG. 8, the imaging pod 800 includes contact pins 805 sized to be received in sockets of the receptacle 755 of the surgical device 190, thereby providing a plug-in type connection. When the imaging pod 800 is inserted in the surgical device 190, the contact pins 805 provide connections to circuitry 760, which supplies power to the appropriate components of the imaging pod 800 and transmits signals from the CCD 725 to a corresponding receiver in the remote device, such as the electro-mechanical driver device 110, through, for example, the surgical device 190 and the flexible shaft 170.

Referring now to FIG. 8b there is seen an exemplary receptacle 755 of the surgical device 190 configured to receive the imaging pod 180. As shown in FIG. 8b, the receptacle 755 includes sockets 810 sized to receive the contact pins 805 of the imaging pod 800. The sockets 810 electrically couple the contact pins 805 to electrical leads (not shown) in the surgical device 190. The electrical leads are electrically connected to the remote device (e.g., the electro-mechanical driver device 110) via wires situated, for example, within the flexible shaft 170 of the electro-mechanical driver device 110.

It should be appreciated that the imaging pod 800 may include a battery for power, and utilize wired transmission for signals from the CCD, or alternatively, receive power via a wired connection and utilize wireless transmission for the signals from the CCD.

Figure 9:
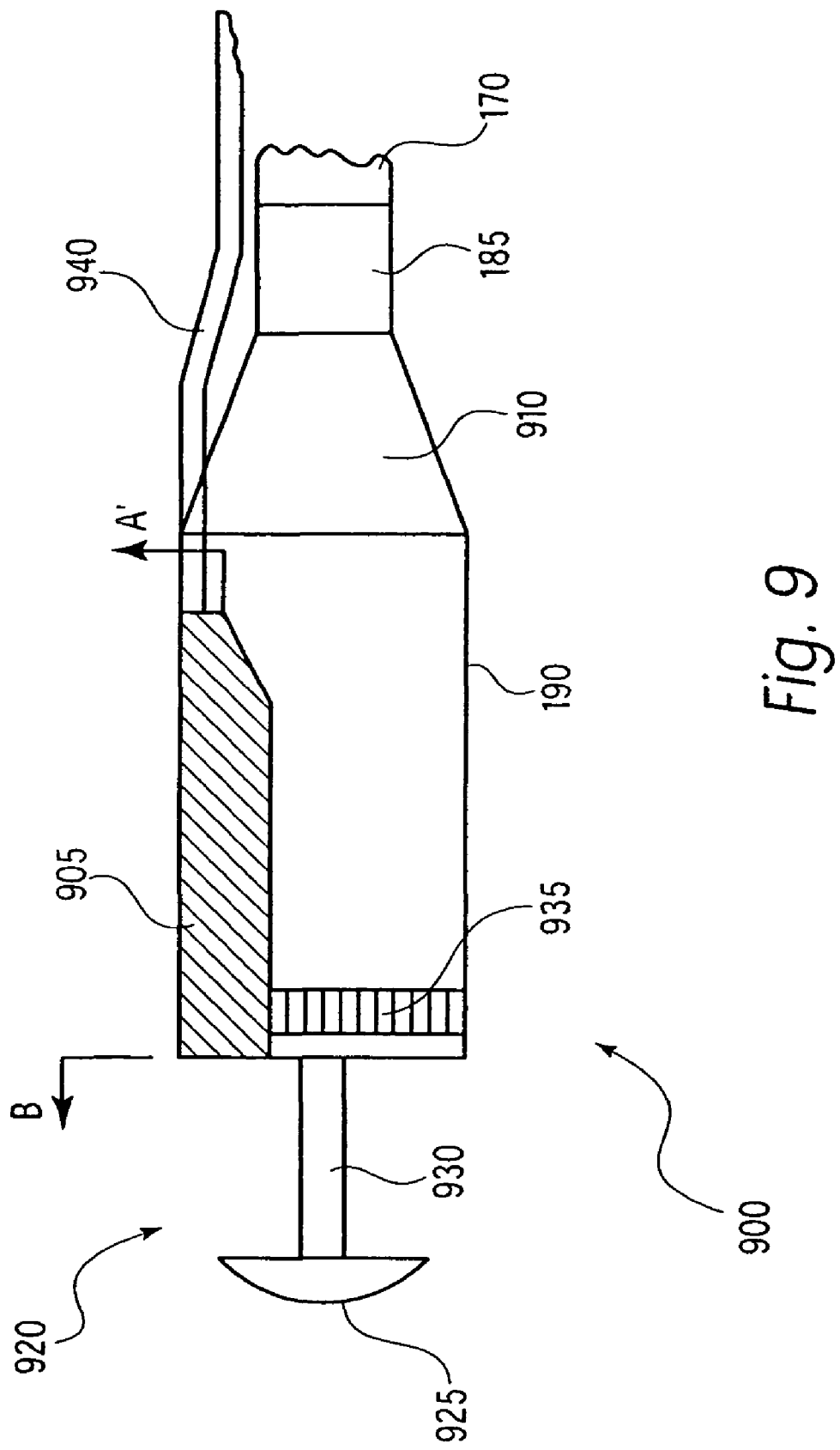
FIG. 9 illustrates another exemplary surgical attachment according to the present invention.

Referring now to FIG. 9, there is seen another exemplary surgical attachment 900. In this embodiment, an imaging device 905 is configured to be coupled to or mounted on an external surface of the surgical device 190. Of course, the imaging device 905 may also be configured to mount on other surgical devices, such as those described in the U.S. applications incorporated by reference above.

In accordance with this exemplary embodiment, the surgical device 190 is a circular surgical stapler. The imaging device 905 is mounted to a body 910 of the surgical device 190. The surgical device 190 includes a coupling 915, an anvil portion 920 and a body 910. The anvil portion 920 includes an anvil 925 and anvil stem 930. A flexible wire assembly 940 is provided for communicating image data to a remote device, e.g., the electro-mechanical driver device 110 (not shown).

The imaging device 905 may slidingly fit over the body 910 and may be either permanently or removably mounted to the body 910. In the example embodiment shown in FIG. 9, the imaging device 905 is removably mounted to the body 910 via a resilient, e.g., plastic or elastic strap 935. Strap 935 may be removed, for example, which may permit the imaging device 905 to be reused with another surgical device or attachment. Alternatively, the imaging device 905 may be mounted to the surgical device 190 via a shoe (not shown) similar to the type used with a flash unit on a camera.

The video unit 100 may be coupled, for example, to a processor via a wireless connection or a wired connection via flexible wire assembly 940. The flexible wire assembly 940 may include power, control and data lines. The flexible wire assembly 940 may be coupled to, for example, a processor of a remote power console as described in, for example, U.S. patent application Ser. No. 09/836,781. Of course, in lieu of the flexible wire assembly 940, the wired connection between the imaging device 905 and, for example, the processor, may be effected via individual wires disposed within or external to the flexible shaft 170 of the electro-mechanical driver device 110.

It should be appreciated that the wires of the flexible wire assembly 940 and/or the wires disposed within or external to the flexible shaft 170 of the electro-mechanical driver device 110 for communicating image data from the imaging device 905 to, for example, the processor, may be replaced with fiber-optic connections.

Imaging device 905 may include analogous features to the imaging devices 300 and 700 described above. For example, imaging device 905 may include an image capture arrangement (e.g., a camera), a circuit arrangement electrically coupled to the image capture arrangement, and a power supply arrangement for supplying power to the imaging device 905.

The image capture arrangement of the imaging device 905 may include a lens, a light source for illuminating an object to be imaged (e.g., fiber optic light sources, light bulbs, LEDs, etc.), an image sensor (e.g., a CCD or CMOS-type image sensor) positioned to capture an image via the lens. In one embodiment, the image capture arrangement of the imaging device 905 may further include a cleaning arrangement for cleaning debris from a lens. Each of the lens, the light source, the image sensor, and the cleaning arrangement may also communicatively coupled to data bus.

What is claimed is:

1. A surgical imaging device comprising:
    a housing configured to detachably electronically couple to a socket arranged at an outer surface at a distal end of a surgical device;
    an image capture arrangement situated in the housing, the image capture arrangement including an image sensor, the image sensor positioned at the distal end of the housing and of the surgical device when the housing is electronically coupled to the socket of the surgical device and during imaging, the image sensor configured to receive an image, generate at the distal end of the housing image data corresponding to the received image and to communicate the image data, wherein the image capture arrangement further includes a light source configured to illuminate an object to be imaged; and
    a strap for coupling the housing to the surgical device.

2. The surgical imaging device according to claim 1, wherein the housing is configured to slidingly couple to the surgical device.

3. The surgical imaging device according to claim 1, wherein the image data generated by the image capture arrangement includes one of still image data and video data.

4. The surgical imaging device according to claim 1, wherein the image capture arrangement includes a lens.

5. The surgical imaging device according to claim 1, further comprising:
    a circuit arrangement disposed within the housing and configured to communicate the image data to at least one remote device.

6. The surgical imaging device according to claim 5, wherein the circuit arrangement is configured to communicate the image data to the at least one remote device via one of wired connection and a wireless connection.

7. The surgical imaging device according to claim 1, wherein the distal end of the surgical device is configured to perform a surgical operation.

8. A surgical attachment comprising:
    a surgical device having an outer surface located at a distal end of the surgical device;
    a surgical imaging device having a housing configured to detachably electronically couple to a socket arranged at the outer surface at the distal end of the surgical device and having an image capture arrangement situated in the housing and configured via an image sensor to receive an image, generate at the distal end of the housing image data corresponding to the received image and to communicate the image data, wherein the image capture arrangement includes a light source, the light source configured to generate light from the distal end of the surgical device when the housing is electronically coupled to the socket of the surgical device and during imaging; and
a strap for coupling the housing to the surgical device.

9. The surgical attachment according to claim 8, wherein the housing is configured to slidingly couple to the surgical device.

10. The surgical attachment according to claim 8, wherein the image data generated by the image capture arrangement includes one of still image data and video data.

11. The surgical attachment according to claim 8, wherein the image capture arrangement includes a lens.

12. The surgical attachment according to claim 11, wherein the image capture arrangement further includes an image sensor positioned to capture an image via the lens.

13. The surgical attachment according to claim 8, wherein the surgical imaging device further includes a circuit arrangement disposed within the housing and configured to communicate the image data to at least one remote device.

14. The surgical attachment according to claim 13, wherein the circuit arrangement is configured to communicate the image data to the at least one remote device via one of wired connection and a wireless connection.

15. The surgical attachment according to claim 8, wherein the light source is a light emitting diode.

16. The surgical attachment according to claim 8, wherein the distal end of the surgical device is configured to perform a surgical operation.

17. A surgical system, comprising:
an electro-mechanical driver device;
a surgical attachment including a surgical device having an outer surface located at a distal end of the surgical device a surgical imaging device, the surgical imaging device having a housing configured to detachably electronically couple to the socket at the outer surface at the distal end of the surgical device and having an image capture arrangement situated in the housing and configured via an image sensor to receive an image, generate at the distal end of the housing image data corresponding to the received image and to communicate the image data, wherein the image capture arrangement includes a power source, the power source positioned at the distal end of the surgical device when the housing is electronically coupled to the socket of the surgical device and during imaging; and
a strap for coupling the housing to the surgical device.

18. The surgical system according to claim 17, wherein the housing is configured to slidingly couple to the surgical device.

19. The surgical system according to claim 17, wherein the image data generated by the image capture arrangement includes one of still image data and video data.

20. The surgical system according to claim 17, wherein the image capture arrangement includes a lens.

21. The surgical system according to claim 20, wherein the image capture arrangement further includes an image sensor positioned to capture an image via the lens.

22. The surgical system according to claim 21, wherein the image capture arrangement further includes a light source configured to illuminate an object to be imaged.

23. The surgical system according to claim 17, further comprising:
a circuit arrangement disposed within the housing and configured to communicate the image data to at least one remote device.

24. The surgical system according to claim 23, wherein the circuit arrangement is configured to communicate the image data to the at least one remote device via one of wired connection and a wireless connection.

25. The surgical attachment according to claim 17, wherein the power source is a battery.

26. The surgical system according to claim 17, wherein the distal end of the surgical device is configured to perform a surgical operation.

27. A method of using and reusing a surgical imaging device, the surgical imaging device including at least two of an image sensor configured to receive an image, generate at the distal end of the housing image data corresponding to the received image and to communicate the image data, a light source for generating light and a power source, the method comprising:
detachably electronically coupling the surgical imaging device to a socket located at a distal end of a first surgical device;
removing and electronically decoupling the surgical imaging device from the socket of the first surgical device;
detachably electronically coupling the surgical imaging device to a socket located at a distal end of a second surgical device, wherein the at least two of the image sensor, the light source and the power source are positioned at the distal end of the surgical imaging device and of the second surgical device when the at least two of the image sensor, the light source and the power source are electronically coupled to the second surgical device and during operation of the second surgical device; and
coupling the surgical imaging device to the respective one of the first and second surgical devices via a strap.

28. The method according to claim 27, wherein each of the steps of detachably coupling the surgical imaging device to the first and second surgical devices includes slidingly coupling the surgical imaging device to the respective one of the first and second surgical devices.

29. The method according to claim 27, further comprising the step of:
generating image data via the surgical imaging device.

30. The method according to claim 29, wherein the image data generated by the surgical imaging device includes one of still image data and video data.

31. The method according to claim 30, further comprising the step of illuminating an object to be imaged.

32. The method according to claim 29, further comprising the step of transmitting the image data to at least one remote device.

33. The method according to claim 32, wherein the step of transmitting includes transmitting by at least one of a wired-connection and a wireless connection.

* * * * *